(12) United States Patent
Ames

(10) Patent No.: US 6,598,992 B1
(45) Date of Patent: Jul. 29, 2003

(54) PORTABLE FOOT INSPECTION MIRROR

(76) Inventor: John Lucius Ames, P.O. Box 6183 (2210 Indiana Ave.), Bradenton, FL (US) 34281

(*) Notice: Subject to any disclaimer, the term of this patent is extended or adjusted under 35 U.S.C. 154(b) by 0 days.

(21) Appl. No.: 10/121,072

(22) Filed: Apr. 12, 2002

(51) Int. Cl.[7] ............................................. F21V 33/00
(52) U.S. Cl. ..................... 362/138; 362/140; 600/248; 600/247
(58) Field of Search .................. 362/138, 139, 362/140; 600/189, 247, 248; 433/30, 31; 359/850, 853, 869

(56) References Cited

U.S. PATENT DOCUMENTS

| | | | | |
|---|---|---|---|---|
| 1,643,626 A | * | 9/1927 | May ........................... | 359/857 |
| 2,136,832 A | * | 11/1938 | Weisberger ................. | 600/248 |
| 4,257,680 A | * | 3/1981 | Baczkowski ................ | 359/879 |
| 4,623,955 A | * | 11/1986 | Santini ....................... | 362/135 |
| 5,043,852 A | * | 8/1991 | Gerstenberger ............. | 362/129 |

\* cited by examiner

*Primary Examiner*—Sandra O'Shea
*Assistant Examiner*—Ronald E. DelGizzi
(74) *Attorney, Agent, or Firm*—Dorothy S. Morse

(57) ABSTRACT

A lightweight, portable foot inspection mirror, and method for its manufacture, with magnification and high intensity lighting sufficient for detailed viewing by a human adult of his or her own foot surfaces from a standing position. The present invention also has an illuminated activation switch configured for easy operation by a toe or other portion of a human foot, timed operation that allows for automatic deactivation of the high intensity lighting at a pre-set time after being switched on, and an optional elongated handle. Although not limited thereto, use of the present invention is particularly suited for foot inspection by diabetics and others interested in frequently monitoring foot health.

20 Claims, 5 Drawing Sheets

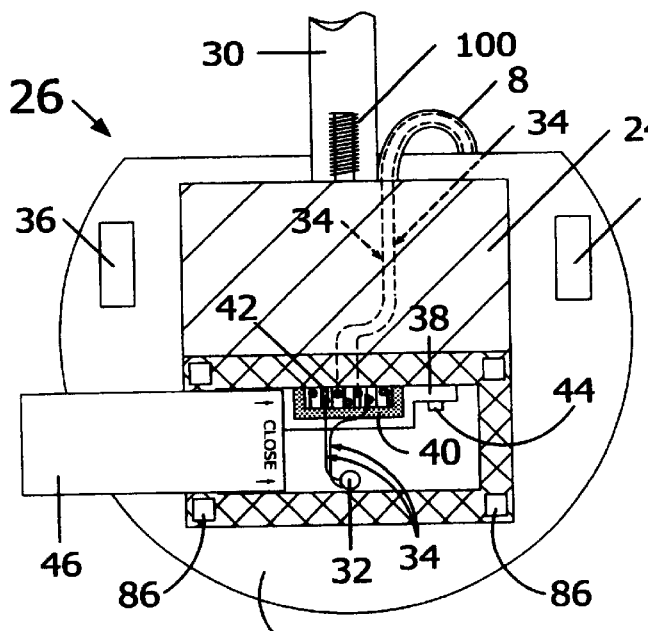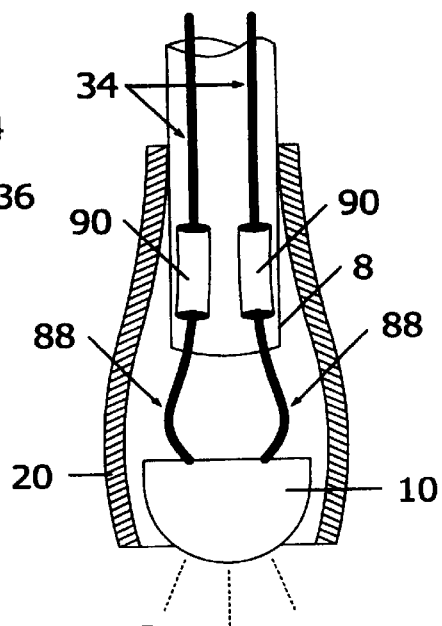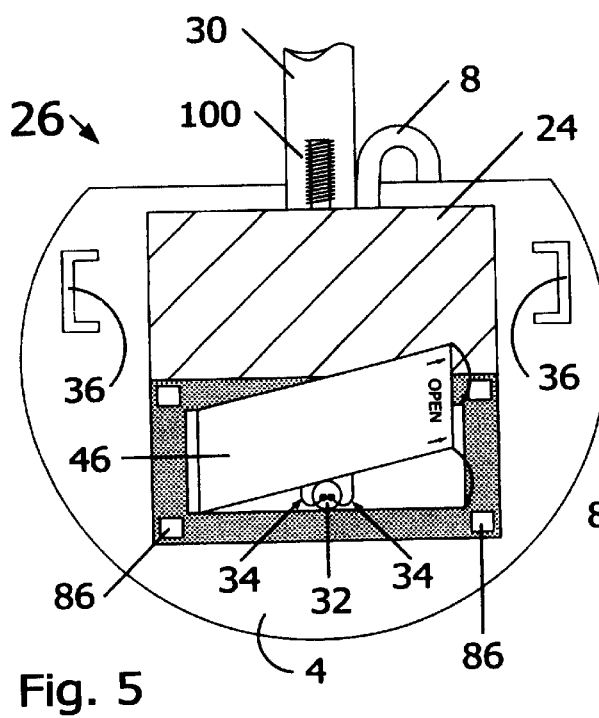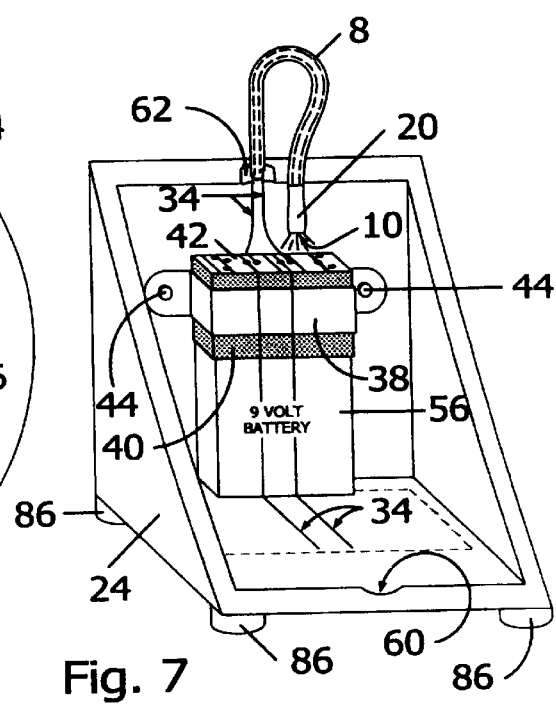

PORTABLE FOOT INSPECTION MIRROR

BACKGROUND

1. Field of Invention

This invention relates to lighted mirrors, specifically to a small, portable, lightweight, and easily maneuverable foot inspection mirror, preferably battery operated but not limited thereto, and a method for its manufacture. The present invention has sufficient magnification and a sufficient amount of high intensity lighting, preferably by using one or more high intensity LED lights, hereinafter referred to as Hi-LED light or lighting, or in the alternative fiber optic lighting, for detailed viewing by a human adult of all of the skin surfaces on his or her own feet from a standing or seated position, without having to lean over or become contorted into uncomfortable positions for enhanced foot visibility. At least one light source stays on at reduced power between uses, so that a person needing to locate the present invention in a dimly lit or darkened room can easily find it. The preferred embodiment of the present invention also has a switch that is illuminated so that it can be promptly located, and is preferably placed in a centered position below its magnified reflective surface. Preferably also, a skin touch switch activated by body electricity is used, which is configured and dimensioned for easy operation by a toe or other portion of a foot whereby the light source used for inspection purposes is promptly brought to full power, although other switch configurations could also be used, to include but not be limited to toggle switches, depressible switches, and optical switches that used interruption of an optical signal to bring the light source to full power. In addition, the present invention has timed operation that allows for automatic power reduction of the light source to approximately two percent or less of its operating intensity, at a pre-set time after it is switched on, to conserve power and minimize the frequency of battery and/or light source replacement. Further, an elongated handle is optional and configured for easy user movement of the magnified reflective surface from one location or spatial orientation to another without the user having to directly touch the reflective surface, or its supporting frame, with his or her hands. The elongated handle can be straight, curved, made from flexible material, detachable, folding, or telescoping. Although not limited thereto, use of the present invention is particularly suited for foot inspection by diabetic adults and others needing to frequently monitor foot health, and for a variety of inspection applications by those who are wheelchair bound, to include inspection of feet and other body parts. Many other industrial and personal inspection applications, such as viewing hidden areas behind or under large and/or difficult to move pieces of equipment or furniture, are also contemplated for the present invention and considered to be within its scope.

2. Description of Prior Art

Healthy feet are important to overall good health, however, they are frequently the object of injury, neglect, and/or abuse. Ill-fitting shoes can cause corns, blisters, and calluses on feet, while bruises, punctures, and abrasions can occur when shoes are not worn. In addition, feet support the entire weight of a person, and when they are sore feet can cause unsuspected changes in posture that over extended periods of time can lead to back pain as well as undue stress on knee and hip joints. Therefore, it is important for all people to regularly inspect the condition of their feet for imperfections, so that what initially may start out as a small cut, blister, skin discoloration, abrasion, or minor skin infection can be treated promptly, before it leads to more serious medical conditions. However, self-inspection of certain parts of the foot, such as the outer rim of a foot, is difficult for many adults to achieve, particularly those who are overweight, less flexible due to injury or disease, those who are wheelchair bound, and those who are exceptionally tall. While most adults can easily view the majority of the skin surfaces on the top and inside portions of their own feet, a clear view of the skin surfaces on the outer rim of each foot, the entire bottom of each foot, and between the toes is more difficult to accomplish. Use of a small and inexpensive hand manipulated mirror in a well-lit room improves foot inspection capability, but can still be awkward and/or place the user in uncomfortable contorted positions. However, the ideal combination of bright illumination positioned close to a foot, optimal rewardly-inclining angle of the reflective surface for enhanced foot viewing by a person in a standing or comfortably seated position, and sufficient magnification in the reflected image, preferably magnification that enlarges the reflected image approximately five times actual size, would greatly facilitate foot self-inspection by all adults. While many types of lighted mirrors are known for applying make-up to the face and for shaving, none is known to have a combination of portability, ease of use, optimal amount of magnification, proper rearwardly inclining angle of the reflective surface, and bright illumination that allows adults to critically inspect scratches, blisters, skin discolorations, irritated areas, and other skin imperfections on their own feet by foot movement in front of a substantially stationary reflective surface, without the user having to lean over or become contorted into uncomfortable positions that would otherwise be required for viewing of all of the skin surfaces on one's own feet with known prior art devices.

SUMMARY OF INVENTION—OBJECTS AND ADVANTAGES

The primary object of this invention is to provide an easy-to-use foot inspection mirror for diabetic adults and others who have an interest in frequently monitoring foot health. It is also an object of this invention to provide a foot inspection mirror with sufficient illumination and magnification for most adults to easily, and without contortion, see all of the skin surfaces of each of their own feet from a standing or comfortably seated position. It is a further object of this invention to provide a foot inspection mirror with a light source that can be activated without employing the operator's hands. It is also an object of this invention for thorough foot inspection to be possible through movement of the operator's feet instead of his or her hands. A further object of this invention is to provide an inspection mirror for human feet that is optionally cordless, easily portable, is made from low maintenance materials, and conserves power for infrequent light source and battery replacement. It is also an object of this invention to provide a foot inspection mirror that is lightweight and easily positioned into the needed spatial orientations for viewing all of the skin surfaces on a human foot. A further object of this invention is to provide an inspection mirror for human feet that is made from durable materials, is cost efficient to manufacture, and is aesthetically appealing. It is also an object of this invention to provide a lighted mirror with magnification that can also be used or adapted for use by adults with limited mobility or flexibility due to injury or disease, those who are wheelchair bound, and other adults simply for the convenience of the viewing other body parts such as the back of an elbow or knee, the face for make-up application, seeing behind large or difficult to move objects, or seeing under pieces of furniture, and for other uses such as by police and customs agents to quickly inspect the underside surfaces of an automobile or truck. A further object of this invention is to provide an inspection mirror for human feet that remains illuminated at reduced power so that it can be easily located in a dimly lit or darkened room.

As described herein, properly manufactured and used, the present invention would enable those adults needing to conduct frequent inspections of their own feet to do so easily and without having to lean over or become contorted into uncomfortable positions. Although the present invention is relatively small and quite maneuverable, its stable base member allows the entire skin surface on each of a operator's own feet to be viewed by foot movement alone, and without the need for hand manipulation of its light source activation switch or its magnified reflective surface during inspection use, unless the user does so by choice. Further, since the most preferred embodiment of the present invention uses one or more Hi-LED or fiber optic lights each positioned close to the reflected surface where it is able to create a diffused source of light, there is sufficient illumination of a foot placed close to the reflective surface, as a result of direct and reflected light on the foot, that an adult can conduct a detailed and critical inspection of the bottom and side surfaces of his or her own feet, from either a standing or comfortably seated position. A highly intense level of brightness is generally preferred for inspection purposes, with a hood extending over most of the light source to direct the bright emitted light toward the magnified reflective surface and keep it from shining into a operator's eyes when the user is looking down at the reflective surface from a standing position, however, when a Hi-LED light is used, it may optionally have a frosted exterior to better diffuse emitted light onto the reflective surface. Also when used, each Hi-LED light is preferably attached to the distal end of a bendable rod or tube, such as a copper rod, so that the angle at which reflected light impacts the reflective surface can be optimally adapted to the intended application. As another option when Hi-LED lighting is used, a removable frosted cap can be temporarily placed over each Hi-LED light source as needed during viewing of facial features, so that the bright Hi-LED lighting does not directly shine into the operator's eyes. The cap could have attachment means adapted for securing it to the bendable rod or tube, or to the frame supporting the reflective surface, so that it does not become separated from the remainder of the present invention and remains readily available when needed for use. Further, although it could be used in any level of ambient light, the present invention works very well in a darkened room. Its switch is sufficiently illuminated so that it can easily be located in reduced light conditions, and at least one light source remains lit at approximately two percent or less power between uses. The switch is preferably activated by body electricity. For most applications, reflecting surface magnification of five times actual size affords users of the present invention some flexibility in adjusting the optimal viewing distance between the reflective surface and the portion of a foot needing inspection. A maximum foot-to-mirror distance of approximately two inches is favored for routine inspection purposes. Due to the concave configuration of the reflective surface, most of the light emitted from each Hi-LED or fiber optic light used, as well as all light reflected back into the mirror, does not travel beyond the perimeter edge of the mirror. Thus, in addition to providing magnification, the shape of the reflective surface helps to focus the light striking it, for better foot viewing.

The height and width dimensions of the most preferred embodiment of the reflective surface are approximately four-and-one-half inches and six-and-one-half inches, respectively, although reflective surfaces with other dimensions are also contemplated. In addition, the base member of the present invention places the supported reflective surface at a rearwardly inclined angle relative to the floor or other support surface beneath it so that an operator can look directly down at the reflective surface and not have to lean over or become contorted into uncomfortable positions to view the reflected images of all of the skin surfaces on his or her foot as it is placed into various orientations in front of the magnified reflective surface. Conveniently, the same rearwardly-inclined angle used for foot inspection is also good for applying make-up, when the present invention is laid upon its back and a frosted cap is used over the Hi-LED light to diffuse emitted light and prevent it from shining directly into a operator's eyes.

The most preferred embodiment of the present invention is also lightweight for easy maneuverability and has a configuration offering users many readily gripped edges and/or contours for easy handling, when hand manipulation is desired. Additionally, handles can be attached to the base member or frame to enhance hand manipulation, including variously configured small handles laterally attached to the base member or frame, and/or one optional elongated handle permanently or detachably connected to the central back portion of the base member or frame. As a result, when an elongated handle is available for use, the present invention could be stored in an out-of-the-way location in a bedroom, bathroom, hotel room, or the like, prior to its use, and then when needed for use, moved into a usable position with the elongated handle. The activation switch, preferably illuminated and also preferably activated via skin contact using body electricity, would subsequently be engaged by a toe or other part of a foot without the user having to lean over, and then the operator's feet, one at a time, would be moved close to the rearwardly inclined reflective surface until all of the skin surfaces on each foot have been viewed. Another activation switch alternative would use interruption of an optical signal to being the light source to full power. Should a portion of the operator's feet require a more detailed viewing, the user could sit down, or in the alternative hold onto a stationary object with one hand for balance, and grasp the elongated handle of the present invention with the remaining hand to place the magnified reflective surface into the proper orientation that allows optimal viewing of any previously hidden skin surfaces or imperfections on the feet. Once viewing is complete, the elongated handle can also be employed to return the mirrored unit back into its out-of-the-way storage location. The configuration of the elongated handle is not critical and could be straight, angled, or curved. For compact storage, or travel purposes, it is contemplated that the handle could be detachable, and/or foldable or telescoping in design. Also, for the convenience of an operator, the elongated handle could be made from flexible material and given a mid-point bending aide strap, to provide the user with enhanced reflective surface maneuverability. Users would not have to remember to turn off the Hi-LED or fiber optic lighting after use, as automatic deactivation would occur after a pre-set period of time following activation, to reduce power consumption and extend the time between battery and light bulb replacement. For simplicity of use, although not limited thereto, it is contemplated that the active time period would be pre-set during manufacture. By way of example, in one preferred embodiment it is contemplated that both a Hi-LED light source having a low power requirement and a long lasting 9-volt battery would be employed. Micro-circuitry would also be employed that provides for automatic deactivation of the Hi-LED light after a predetermined time period of approximately two to three minutes, to maximize power conservation and minimize the need for battery and/or light bulb replacement in the present invention, so that battery replacement might only be needed once a year when the present invention is employed by a single person and limited to foot inspection purposes. In the alternative, lower cost and less technically sophisticated embodiments, that might require more frequent battery exchange, can be made using one or more incandescent light sources in combination with different types or sizes of batteries. However, when incandescent lighting is used it generates heat, and additional safety precautions would be taken to protect feet moving close to the reflective surface from being exposed to excessive amounts of heat. Also, embodiments having a power cord for use with alternating current power sources are considered within the scope of the present invention. For those preferred embodiments of the present invention using direct current, prompt and easy battery exchange can achieved when its power conserving micro-circuitry is incorporated into the top end of a cap configured and dimensioned for fitting closely over the electrically active end of a 9-volt battery. It is contemplated for one of the sides of the cap to be firmly fixed against the inside surface of the base member. Thereafter, when the 9-volt battery needs replacement, it can simply be withdrawn from the cap, followed by full insertion and firm seating of the electrically active end of a replacement 9-volt battery within the hollow interior of the cap. No additional battery connection steps would be required and the replacement would be quickly accomplished. The battery cap and base member can be manufactured as a single unit through molded construction, which is preferred, or secured to the base member after manufacture in a number of ways, such as through the use of a mounting bracket. It is contemplated that the frame and base member in the most preferred embodiment of the present invention would be made from lightweight durable materials, such as plastic, and for the light source use to be unobtrusively positioned, so as not to interfere with movement of a foot as it is placed into various orientations in front of the magnified reflective surface during skin surface inspection. As a further option, the frame can be attached to the base member by a swivel connection. Floor-gripping support feet can also be attached to the bottom surfaces of the base member and or frame to help maintain the reflective surface in a stationary position during use. As a result, it is contemplated for the light source used to either comprise one or more curved rods or tubes each supporting a Hi-LED light, or in the alternative tiny stalks of fiber optic lighting, mounted so as to shine into the magnified reflective surface from a superimposed position, while the base member supports the reflective surface optimally at a rearwardly reclined angle during use. A second light source option would be to provide one or more recessed high-intensity LED, fiber optic, or incandescent light sources in recessed positions adjacent to the reflective surface, behind frosted glass or panels made from other materials that are able to diffuse the emitted light and prevent it from shining directly in the eyes of a person using the magnified reflective surface for inspection purposes, such as when the present invention is used to view a portion of a human face. A third light switch option would be to provide both superimposed light sources in combination with others recessed behind frosted panels, with switching capability that allows alternative or combined use, to diversify applications of the present invention. Although either Hi-LED or high intensity incandescent light sources could be used, Hi-LED or fiber optic lights would be preferred in applications where heat generation is a concern. Hi-LED and fiber optic lighting would not become hot and would be safe to touch, particularly since it is preferred that the light source to remain continuously lit at approximately two percent or less power when not in use so that people can easily locate it in a dimly lit or darkened room and see the area adjacent to the reflective surface that must be contacted to activate the light source.

Also, the frame and base member can be made as two separate pieces and combined during manufacture, or made a single piece through molded construction. The frame and base member should be combined in a way that allows for easy user access to the 9-volt battery so that it may be promptly and easily replaced without interfering with the positioning of the Hi-LED or fiber optic lighting relative to the reflective surface, or connection of any electrical wiring extending between the light source, the activation switch, and the battery cap. Further, the materials from which the present invention is made are not critical, and any cost effective, easily cleaned, and durable material for the frame and base member that is also light in weight, such as plastic, is considered to be within the scope of the present invention. Also, the present invention is not limited to having one reflective surface and one base member. Multiple reflective surfaces can be used that are attached to a single support, or they can each have an individual support that is connected to adjacent supports for stability during use. Further, multiple-piece supports can be used for any reflective surface such as but not limited to several rearwardly extending legs that can be optionally attached together with laterally extending connection members or a webbed structure. However, no matter what type of support is used, the design of the support and it connection to a reflective surface should not restrict access to any battery compartment present. Whether a battery compartment is contained within a one-piece base member or concealed within a handle or a rearwardly extending leg, it should be prompt and easy to access. Therefore, to provide battery compartment access it is contemplated that the connection between support and reflective surface could consist of many options, including but not limited to a hinged connection between a frame and a base member so that one opens away from the other to reveal the battery compartment; a cover having a snap-in type of closure over an opening through the back of a base member, handle, or leg; a sliding cover used to seal an opening through a base member, handle, or leg; or any other means of direct access to the battery compartment that is cost efficient to construct and easy to operate. With its elongated width, small size, the stability given to the present invention by its low overall height, its upwardly facing and rearwardly reclined reflective surface, and its optional elongated handle, the present invention is aesthetically appealing and unobtrusive. Further, if the associated handle were made to be detachable, telescoping, or foldable, the present invention could be readily packed for travel, where in addition to foot inspection use it could also double as a make-up application or shaving mirror. Since the most preferred embodiment is cordless, being operated by a 9-volt battery, application of the present invention does not require the use of an extension cord for operation remote from electrical outlets or require an operator to lean over to plug it in. Further, since it is lightweight and easily maneuverable, and comprises magnification capability, the present invention can also be used for many non-foot inspection purposes, such as seeing behind large objects, under pieces of furniture, under automobiles, for make-up application use, as well as for a detailed inspection of the skin surfaces on other parts of the body including the back of knee, the back of an elbow, the lower back or buttocks area, and the genital area. No lighted mirror is known with all of the advantages of the present invention.

The description herein provides the preferred embodiment of the present invention but should not be construed as limiting-the scope of the lighted foot inspection invention. For example, variations in the height and width dimensions of the reflective surface; the configuration of reflective surface used, such as curved perimeter, angular perimeter, multiple mirror configuration, or other; the amount of magnification used; the type of light source used; the variety of lighting patterns used; the size and configuration of the preferred touch switch, easily depressible switch, optical interruption switch, or other system activation micro-switch used; the type of illumination used for the activation switch; the length and cross-sectional dimensions of the handles used; the type and configuration of easy manipulation features incorporated into the handles such as straps, ridges, or handles grips with finger indentations; the orientation of the battery when mounted within the base member or a support leg; and the type and size of battery compartment access panel or cover used for battery exchange, other than those variations shown and described herein may be incorporated into the present invention. Thus the scope of the present invention should be determined by the appended claims and their legal equivalents, rather than being limited to the examples of features and uses given herein.

BRIEF DESCRIPTION OF THE DRAWINGS

FIG. 4 is a bottom view of the second preferred embodiment of the present invention having a frame, a base member connected centrally to the back of the frame causing it to be rearwardly inclined, the proximal end of an elongated handle secured to the base member with a threaded stud, two rectangular-shaped protrusions attached to the frame on opposite sides of the base member for use as gripping surfaces or handles, an opening in the base member revealing a battery cap being supported by a bracket, an activation switch, electrical wires connected between the battery cap and the activation switch, a sliding cover, the proximal end of a curved rod or tube connected to the top of the base member, and four floor-gripping support feet connected to the base member.

FIG. 5 is a bottom view of the second preferred embodiment of the present invention having a frame, a base member connected centrally to the back of the frame that positions the frame in a rearwardly inclined position, the proximal end of an elongated handle secured to the base member with a threaded stud, two handles attached laterally to the frame on opposite sides of the base member, the proximal end of a curved tube or rod connected to the top of the base member, and a partially opened cover over an opening in the base member revealing an activation switch and electrical wires connected to the activation switch.

FIG. 6 is an enlarged sectional view of the Hi-LED light of the most preferred embodiment of present invention positioned substantially within the distal end of a hood with only a small portion of one end of the Hi-LED light exposed beyond the end of the hood, electrical wires depending from the opposed hidden end of the Hi-LED light, a bendable rod or tube and electrical wiring both positioned within the proximal end of the hood, with insulating sleeves, bonding material or shrink wrap material securing an electrical connection between the electrical wires attached to the Hi-LED light and the electrical wiring within the proximal end of the hood.

FIG. 7 is view of the interior of the base member of the second preferred embodiment of the present invention, with floor-gripping support feet attached to the bottom corners of the base member, a curved rod or tube positioned within an indentation centrally in the top rear edge of the base member, a Hi-LED light supported by the distal end of the tube or rod, a hood surrounding the Hi-LED light, a battery secured within a cap attached to the inside surface of the base member under the indentation by a bracket and fasteners, with a first pair of electrical wires being connected between the electrical circuitry on the top of the battery cap and the Hi-LED light, and a second pair of electrical wires being connected to the micro-circuitry on the top of the cap and extending downward toward the semi-circular depression in the front lower edge of the base member into which an activation switch would be positioned when the present invention is fully assembled.

DETAILED DESCRIPTION OF PREFERRED EMBODIMENTS

Figure 1:
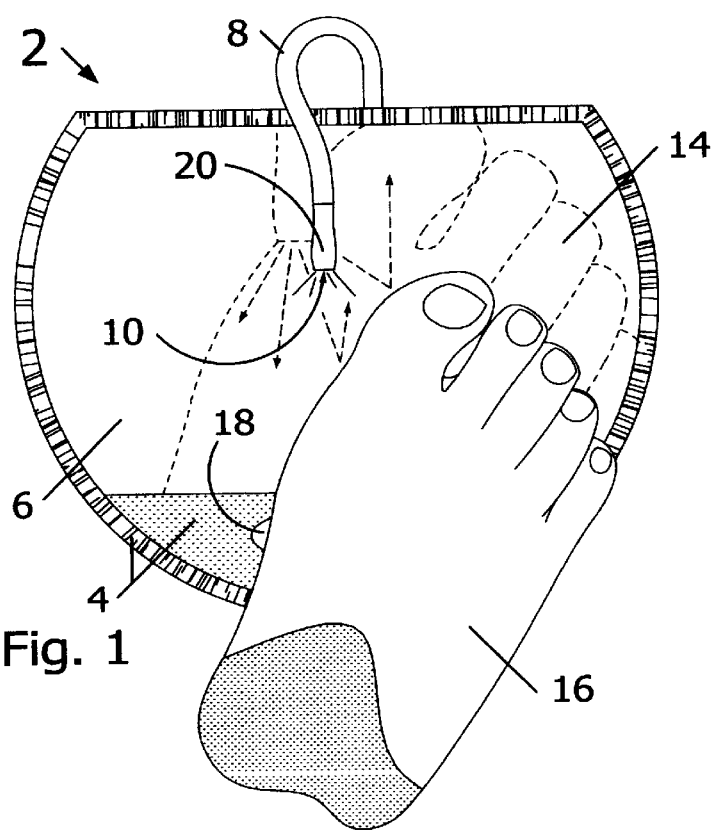
FIG. 1 is a front view of a first preferred embodiment of the present invention having a human foot positioned in front of a magnified reflective surface, a frame around the perimeter of the reflective surface, one small Hi-LED light connected to the distal end of a curved rod or tube the proximal end of which is attached behind the reflective surface, a hood extending substantially over the Hi-Led light to shield a operator's eyes from emitted light and focus light toward the reflective surface, the Hi-LED light being in a superimposed position above the reflective surface to direct light in a downward position toward it as well as onto the human foot, with arrows showing some of the reflected light enhancing illumination of the foot, and a switch positioned on the frame, partially behind the foot, that is illuminated and activated by body electricity for stepping up to full power the intensity of the Hi-LED light.
Figure 2:
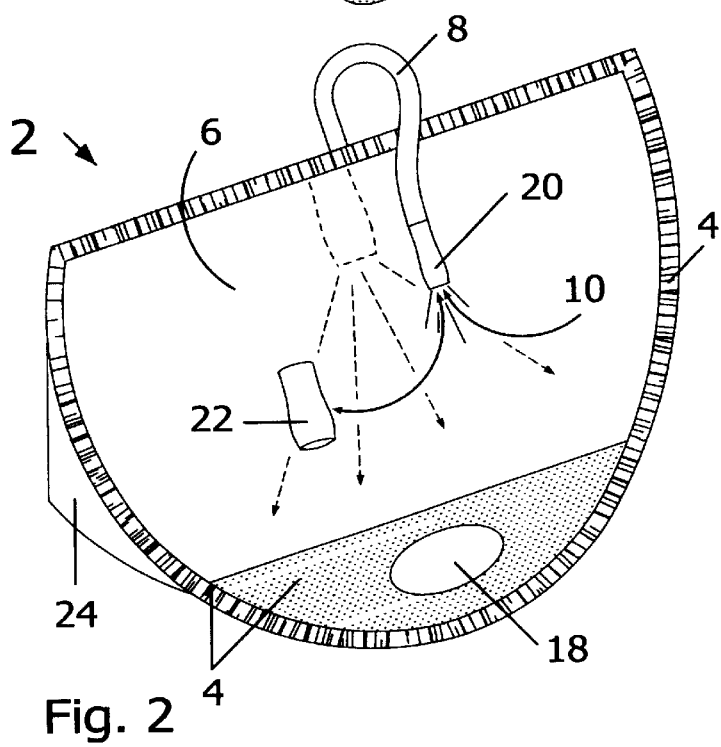
FIG. 2 is a perspective view of the first preferred embodiment of the present invention having a magnified reflective surface, a supporting frame for the reflective surface, rounded base member supporting the reflective surface and frame combination in a rearwardly inclined position, one Hi-LED light in a superimposed position over the reflective surface to direct emitted light in a downward position toward the reflective surface, a hood extending substantially over the Hi-LED light, a skin-touch activation switch centrally positioned on the frame below the reflective surface, the switch being activated by body electricity and illuminated so that an operator can find the present invention in a darkened room and immediately know where to contact the present invention to turn it on, with arrows showing the general direction of reflected light, and a frosted cap poised for optional use over the Hi-LED light and/or hood to further diffuse emitted light and prevent direct contact between it and a operator's eyes, during such applications as when the present invention is laid upon its back and made to double as a make-up mirror during travel.

FIGS. 1 and 2 show a first preferred embodiment 2 of the present invention having a magnified reflective surface 6, a frame 4 surrounding the perimeter of reflective surface 6, one small high intensity Hi-LED light 10 connected to the distal end of a curved rod or tube 8 the proximal end of which is connected to frame 4 behind reflective surface 6, with Hi-LED light 10 being directed to emit light in a downward position toward reflective surface 6. First embodiment 2 is not limited to a Hi-LED light, and fiber optic lighting is also contemplated, which would give first preferred embodiment 2 the same overall appearance shown in FIGS. 1 and 2. Therefore, hereinafter, the term Hi-LED light 10 may be substituted for the term Hi-LED or fiber optic light 10, as well as the reverse. Rod or tube 8 can be rigidly formed during manufacture into a configuration having a fixed radius of curvature, or it can be flexible for operator bending into various curved configurations during use of reflective surface 6, however, when a bendable rod or tube 8 is used, it should have sufficiently rigidity to maintain any position relative to reflective surface 6 operator-selected for Hi-LED or fiber optic light 10. Further, rod or tube 8 is preferably made from copper, although not limited thereto, which would permit movement of Hi-LED light 10 into a variety of configurations. Magnification and high intensity lighting are important to first embodiment 2, since diabetic patients, who are contemplated operators of the present invention, can have impaired visual ability, neuropathy (impaired tactile sensing), or both, making it easy for them to miss important cuts and foot abrasions when they conduct inspections of their own feet, relying only on touch and their unaided eyesight. The length of rod or tube 8 may also vary in different preferred embodiments of the present invention, with FIG. 1 showing a shorter rod or tube 8 that would probably remain fixed in position relative to frame 4, and FIG. 2 showing a longer rod or tube 8 that could be movable by an operator into various positions relative to frame 4. It is also considered to be within the scope of the present invention for rod or tube 8 to have some flexibility so that it will not break when inadvertently contacted by human foot 16 during routine foot inspection. FIG. 1 also shows a human foot 16 positioned in front of reflective surface 6, whereby observation of all surfaces on human foot 16 can be made by either moving human foot 16 relative to reflective surface 6, or in the alternative moving reflective surface 6 relative to human foot 16. It is contemplated that foot 16 would be illuminated by both direct and reflected light originating from Hi-LED light 10. Arrows in FIG. 1 show some of the reflected light striking foot 16. FIGS. 1 and 2 also show a hood 20 connected to the distal end of rod or tube 8. Although not clearly shown in FIGS. 1 and 2 due to the small size of Hi-Led light 10 in each illustration, Hi-LED light 10 does not extend significantly beyond the distal end of hood 20. The preferred positioning of Hi-Led light 10 can be more clearly seen in FIG. 6. When Hi-LED light 10 is recessed within hood 20 with only a small portion of its distal end exposed, the illumination from Hi-LED light 10 becomes diffused and is not limited to a point source that would be ineffective in illuminating a broad area of foot 16. Hi-LED or fiber optic light 10 in preferred over incandescent lighting, as Hi-LED and fiber optic light 10 does not become hot and is safe to touch. Further, it is contemplated for the Hi-LED or fiber optic light 10 to stay on at approximately two percent or less power when not in use, so that when it is stored in a dimly lit or darkened room, those needing it can easily locate it for use. FIG. 6 also shows Hi-LED light 10 being connected to electrical wires 34 by the insulating sleeve or shrink wrap material 90. Although not shown in FIG. 6, it is contemplated for additional insulating sleeve or shrink wrap material 90 to protect rod or tube 8 and electrical wires 34 between hood 20 and the power supply shown in FIGS. 4 and 7 as battery 56, so as to enable electrical operation of Hi-LED light 10. As an alternative to the use of insulating sleeve or shrink wrap material 90, Hi-LED light 10 and hood 20 could be formed as a molded unit, so that both are replaced when Hi-LED light 10 no longer functions. In addition, FIG. 2 shows a frosted cap 22 that could be used over Hi-LED light 10 and hood 20 in selected applications of first preferred embodiment 2 where needed to prevent Hi-LED light 10 from shining directly into an operator's eye's. Although FIGS. 1 and 2 show a single Hi-LED light 10 being used in first preferred embodiment 2, and it is contemplated for a single Hi-LED light 10 to be adequate for most foot inspection uses, as shown in FIGS. 9–11, and 14, it is considered within the scope of the present invention for more than one Hi-LED light 10 to be provided on the end of the same or different rods or tubes 8, as well as for one or more Hi-LED lights 10 to be placed behind frosted panels 68, positioned adjacent to the top and bottom, or opposing sides, of reflective surface 6 to create a bright source of diffused light sufficient for viewing foot skin surfaces from a standing position. Although not shown, one light source can also be used behind frosted panels 68, with its light being split via fiber optics into many separate pieces for illumination of several surfaces of human foot 16 at once. In the alternative, high intensity incandescent lighting (not shown) could also be used behind panels 68 with provisions being taken to dissipate heat generated thereby. Further, as is shown in FIG. 1 by the enlarged reflected image 14 of foot 16, reflective surface 6 is capable of magnification. Although not limited thereto, preferred magnification is capable of causing reflected images 14 that are approximately five times actual size. Also, FIGS. 1 and 2 show most of the reflected light being focused by reflective surface 6, and remaining within the perimeter of reflective surface 6. FIGS. 1 and 2 also show reflective surface 6 having a width dimension that is greater than its height dimension, so that a large portion of foot 16 can be viewed at one time. A reduced height dimension and a wide base also give the present invention a lowered center of gravity and allow it to be more stable during use, so that it is not likely to tip over as a result of casual contact with human foot 16.

Figure 14:
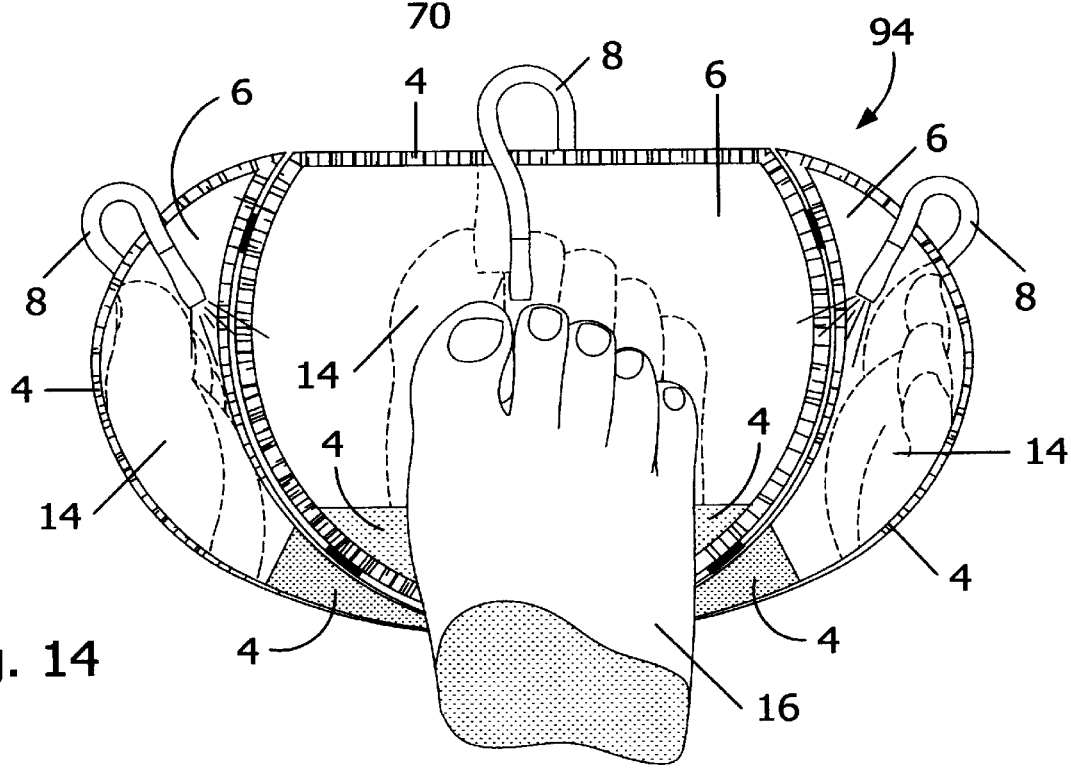
FIG. 14 is a front view of an eighth preferred embodiment of the present invention having three adjoining magnified reflective surfaces, each supported by a base member at a rearwardly inclined angle, the proximal end of a Hi-LED or fiber optic light attached behind each frame so that the distal, ends of the lights are positioned to emit light in a downward direction toward the adjacent reflective surface, and a human foot positioned between the three reflective surfaces.

Although partially obscured by foot 16 in FIG. 1, but visible in FIG. 2, the present invention has an activation switch 18 located centrally on frame 4 near to the bottom perimeter of frame 4. Further, although activation switch 18 is shown as a skin-touch switch in FIG. 2 wherein the electrical body energy of the operator would be the means for powering up Hi-LED light 10, and the skin-touch type of activation switch 18 would be preferred as it is most easily operated by disabled and wheelchair bound adults (not shown), the type, dimension, and/or configuration of switching means used for activation switch 18 is not critical, and it could be larger than that shown in FIG. 2, or have a different configuration such as that of a small depressible button identical or similar to depressible activation switch 32 shown in FIG. 3, a toggle switch (not shown), or an optical switch that functions through interruption of an optical signal. In addition, even though not critical, since it is contemplated for activation of Hi-LED light 10 to be performed in most instances by foot 16, it is preferred for the location of activation switch 18 to be centered near the bottom perimeter of frame 4 for most stable use of first preferred embodiment 2. Although not illustrated in FIG. 1 or FIG. 2, the stability of first preferred embodiment is enhanced by the lower front edge of frame 4 touching the floor surface upon which base member 24 is supported, to prevent frame 4 from moving forward during activation of switch 18 by a toe, heel, side, or other part of human foot 16, and also to prevent easy rear movement of frame 4 away from human foot 16 as a result of casual contact. Also, FIGS. 1 and 2 show a portion of frame 4 extending upwardly from its lower perimeter on either side of activation switch 18 to support it. The amount of frame 4 surrounding switch 18 is variable, and could be larger or smaller than that shown in FIGS. 1 and 2. Further, the portion of frame 4 around activation switch 18 can comprise a variety of decorative shapes, different surface textures, varying graphic images and surface designs, as well as written information. Since it is contemplated for the present invention to be used in a bathroom where water may be present, battery operation is preferred to avoid a risk of electrocution. Also, frame 4 can be positioned at a spaced-apart distance from the bathroom floor supporting it by use of the several floor-gripping support feet shown in FIGS. 4 and 7 by the number 86, which are configured to resist movement of frame 4 relative to human foot 16 inadvertently caused by contact of foot 16 with frame 4 while foot 16 is being placed into various orientations relative to reflective surface 6 during foot inspection applications. Preferably, activation switch 18 would be illuminated, so that operators can easily find it with a toe or side of the foot when using the present invention in a dimly lit or darkened room (not shown). Micro-circuitry connected to battery 56, shown in FIG. 8 as a part of the top end 42 of a battery cap 40, would control activation and de-activation of Hi-LED or fiber optic light 10 in first preferred embodiment 2 between a resting mode of approximately two percent or less power and full intensity. In all battery-operated and alternating current embodiments, as long as power source connection is maintained, it is contemplated that Hi-LED or fiber optic light 10 would always remain on at approximately two percent or less power for easy invention location in darkened rooms where inspection could take place, and be ready for powering up to full intensity as soon as activation switch 18 is engaged. The micro-circuitry on the top end 42 of battery cap 40 would also return Hi-LED light 10 after a pre-determined time period to its two percent or less power level, the time period prior to such de-activation preferably being approximately two to three minutes. It is also considered to be within the scope of the present invention for activation switch 18 to be luminous so as to assist a person in easily locating activation switch 18 with a toe or other portion of foot 16 when the present invention is optionally used in the dark. An illuminated activation switch 18 would particularly assist persons with diabetes whose eyesight can be diminished by the disease. In addition, FIG. 2 shows reflective surface 6 being in a rearwardly inclined position, supported by base member 24. Although base member 24 is shown in FIG. 2 with a rounded configuration, the configuration of base member 24 is not critical and base member 24 can have any configuration that maintains reflective surface 6 in a rearwardly inclined, stable, and low-to-the-ground position. Further, although particularly suited for foot inspection use, the present invention could also be used for other applications, such as seeing behind large objects, under furniture or appliances, under automobiles, viewing other parts of the human body, and when laid on its back being used as a shaving or make-up mirror with optional use of cap 22 so that the bright Hi-LED or fiber optic light 10 does not directly shine into the operator's eyes. The configuration of frame 4 and reflective surface 6 is not limited to the semi-circular shape shown in FIGS. 1 and 2, and it is also considered within the scope of the present invention for frame 4 and reflective surface 6 to be oval, round, hexagonal, or any other configuration that would allow an operator to easily accomplish inspection surveys of the entire skin surface of his or her own foot 16. Although not shown in FIGS. 1 and 2, it is contemplated to have floor-gripping support feet, such as those shown in FIG. 7 by the number 86, attached to the bottom surface of base member 24. So that frame 4 does not easily move away from an operator when casual contact is made between an operator's foot 16 and the magnified reflective surface 6 or frame 4, it is contemplated for floor-gripping support members 86 to be made from high friction material, such as rubber. Multiple frames 4 can also be connected to one another, as shown in FIG. 14 to maximize viewing and minimize movement of foot 16 during inspection. The advantage of the present invention is its small, unobtrusive size relative to the large amount of viewing capability available through its use.

Figure 3:
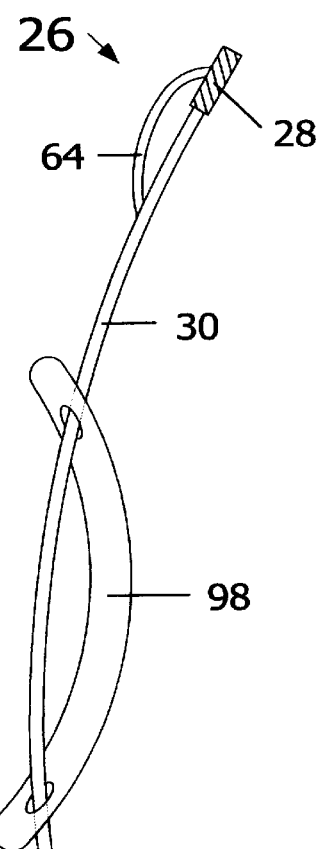
FIG. 3 is a perspective view of a second preferred embodiment of the present invention having an upwardly facing magnified reflective surface, a frame around the perimeter of the reflective surface, a base member supporting the reflective surface and frame combination in a rearwardly reclining angle, an activation switch centrally positioned on the frame below the reflective surface, one small Hi-LED light connected to the distal end of a curved rod or tube the proximal end of which is connected behind the reflective surface, the Hi-LED light being directed to emit light in a downward position toward the reflective surface, an elongated flexible handle connected behind the reflective surface, a mid-point bending aide strap centrally engaging the elongated handle, and a second strap connected to the distal end of the elongated handle for use by those with diminished hand strength making them unable to squeeze the distal end to maneuver it.
Figures 8A, 8B, 8C:
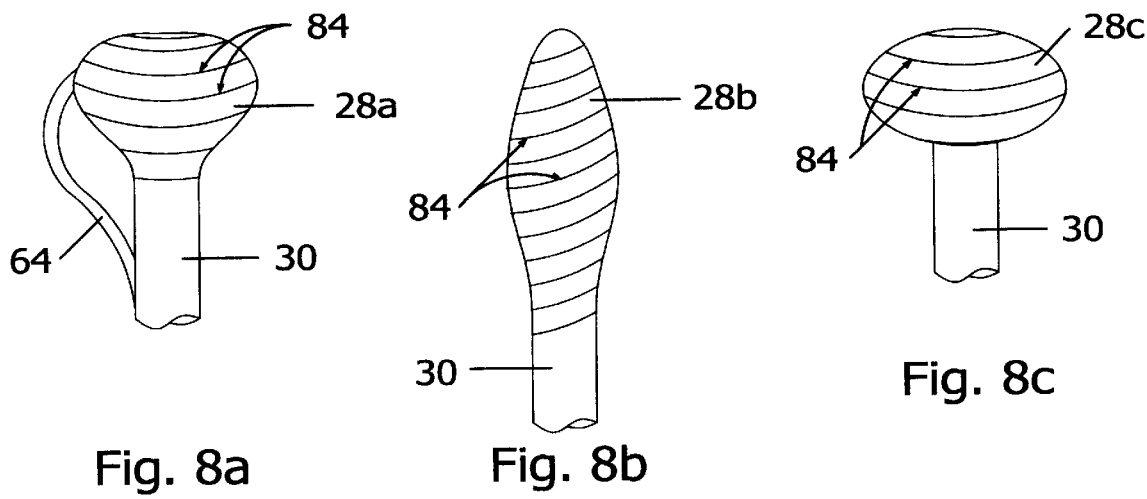
FIGS. 8a–8f are plan views that illustrate some of the different handle grip configurations contemplated by the second preferred embodiment of the present invention for making the present invention more maneuverable by the disabled and others not having full function of their fingers or hands, with optional ridges configured for enhanced grip, a strap providing an opening through which an injured or arthritic hand unable to fully close around a handle can support the present invention, and finger indentations that assist hand manipulation.
Figures 8D, 8E, 8F:
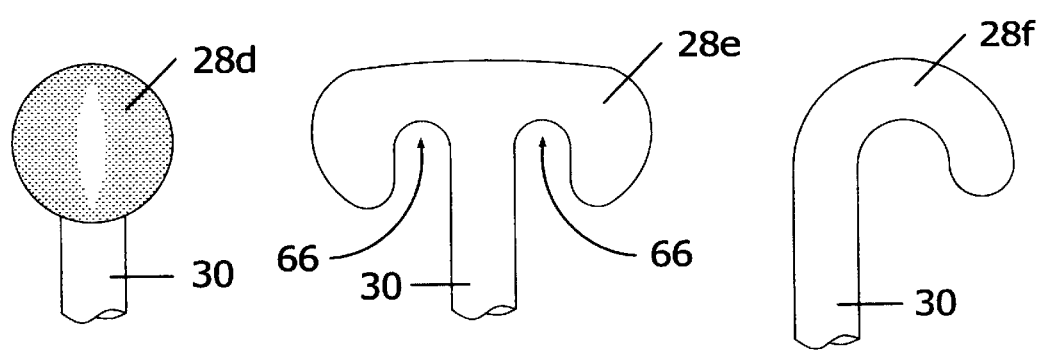

FIG. 3 shows a second preferred embodiment 26 of the present invention having a is magnified reflective surface 6, a frame 4 situated around the perimeter of reflective surface 6, a base member 24 supporting both reflective surface 6 and frame 4 in rearwardly reclining positions, a depressible activation switch 32 positioned on frame 4 in a centered position below reflective surface 6, and one small high intensity Hi-LED light 10 connected within a hood 20 on the distal end of a curved and/or bendable rod or tube 8, the proximal end of which is connected to frame 4 or base member 24 behind reflective surface 6, with the hood 20 around Hi-LED light 10 creating diffused illumination from Hi-LED light 10 that is directed in a downward position toward reflective surface 6. FIG. 3 also shows preferred embodiment 26 having an elongated handle 30 the proximal end of which is connected behind frame 4 or base member 24. Although not shown, in alternative embodiments of the present invention elongated handle 30 could be detachable, folding, telescoping, or have a more elaborate retractable configuration to provide for compact storage or travel. However, the additional complexity in elongated handle 30 is not a critical component of the present invention. Further, although the length of elongated handle 30 is usually sufficient for a human adult operator to use it from a standing position for foot inspection purposes, and although not shown, it is also contemplated for the present invention to comprise a shorter handle in place of elongated handle 30, where needed for added convenience in hand inspection use. The grip 28 on the distal end of elongated handle 30 is shown in FIG. 3 to have a substantially cylindrical configuration. However, the configuration of grip 28 is not critical, as long as an adult human hand (not shown) can easily grasp it, even a hand that is not fully functional as a result of injury or disease. A grip-enhancing strap 64 can also be attached to the distal end of elongated handle 30 so that an operator's hand does not have to be fully enclosed around grip 28 to lift or manipulate the orientation of reflective surface 6. In addition, the grip of an operator's hand may be enhanced by handle grip 28 when it optionally has a design incorporated into it that creates surface texture, such as ridges 84, or a separable sleeve made from high friction material, such as rubber (not shown). As can be seen in FIG. 8, it is contemplated for handle grip 28 to have other configurations, such as but not limited to that of an inverted pyramid as shown in FIG. 8a, a vertically extending oblate spheroid shape as shown in FIG. 8b, a flattened horizontally extending oblate spheroid shape as shown in FIG. 8c, a sphere as shown in FIG. 8d, a T-shape with finger indentations as shown in FIG. 8e, or an inverted J-shape as shown in FIG. 8f. Any configuration of handle grip 28 that allows the present invention to be easily grasped for lifting and transport, or to be easily moved from one spatial orientation to another for improved foot inspection, is considered to be within the scope of the present invention. Elongated handle 30 would also be required for those who are wheelchair bound, since the angle of reflective surface 6 that is optimal for viewing a foot 16 from a standing position may not always be appropriate for viewing a foot 16 from a seated position. A mid-point bending strap 98 can also be attached to a flexible elongated handle 30 to make it more convenient for wheelchair and other use. Floor-gripping support feet 86, not shown in FIG. 3 but as shown in FIGS. 4 and 7, could be attached to the bottom surface of frame 4 and/or base member 24 to prevent elongated handle 30 from moving away from an operator's hand as a result of casual hand contact by a wheelchair bound or other person reaching for it and not initially being able to fully grasp it.

Figure 12:
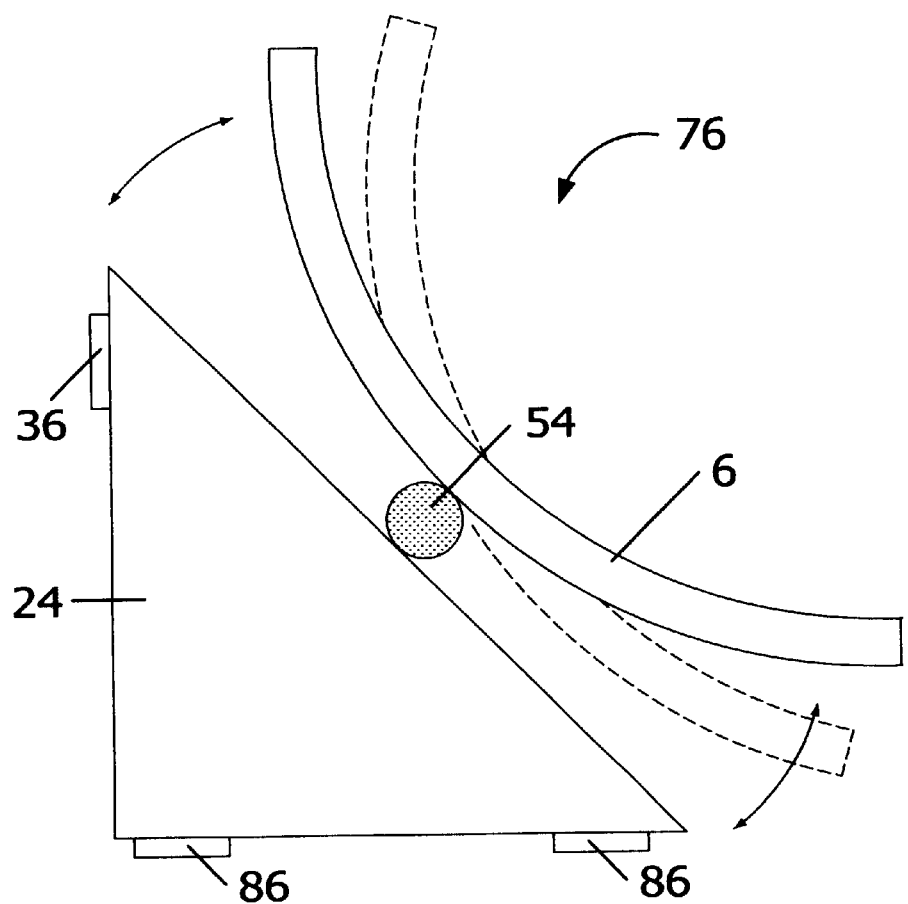
FIG. 12 is a side view of a sixth preferred embodiment of the present invention having a base member, two with a rearward protrusion configured for use as a gripping surface or handle, gripping feet attached to the bottom surface of the base member, a reflective surface, and a swivel joint attached between the reflective surface and the base member for positioning the reflective surface in a variety of orientations relative to the base member.

FIGS. 4 and 5 show the second preferred embodiment 26 of the present invention having a frame 4, a base member 24 connected centrally to the back of frame 4, and the proximal end of an elongated handle 30 secured centrally into the top of base member 24, through the use of a threaded stud 100. Although not shown, other conventional means of connecting elongated handle 30 to base member 24 or frame 4 are also considered to be within the scope of the present invention. FIG. 4 also shows an opening in base member 24 that reveals a battery cap 40 with a top end 42, shown in FIG. 7 as covering the electrically active end of a 9-volt battery 56 and top end 42 incorporating micro-circuitry on its top surface. FIG. 4 further shows cap 40 being supported against the inside surface of base member 24 by a mounting bracket 38 and mounting bracket 38 being attached to base member 24 through the use of a fastener 44. Although hidden by sliding cover 46, it is contemplated for a second fastener 44 to be used for connecting the hidden end of mounting bracket 38 to base member 24. Also, the type of fastener 44 used would depend upon the materials selected for mounting bracket 38 and base member 24, and is not limited to that shown in FIGS. 4 and 7. As an example, it is considered within the scope of the present invention for fasteners 44 to comprise any type of fastener, adhesive, or bonding compound, alone or in combination, that would securely affix mounting bracket 38 to base member 24. In the alternative, and preferred for most applications, cap 40 would be a molded part of base member 24 and require no fasteners 44. The mounting of battery 56 within base member 24 is not limited to the positioning or orientation shown in FIG. 4 and FIG. 7, and any positioning, horizontal or vertical, that allows for easy replacement of battery 56 can be used, whether within base member 24 or within one or more of legs 72, as shown in FIG. 12. FIG. 4 further shows electrical wires 34 being connected between the top end 42 of cap 40 and depressible activation switch 32 located adjacent to the central bottom perimeter of base member 24, and additional electrical wires 34 being connected to the top end 42 of cap 40 and following curved rod or tube 8 for attachment to Hi-LED light 10, which is hidden in FIG. 4. The proximal end of rod or tube 8 can be connected to either the top of base member 24, or the upper rear portion of frame 4. Although not critical, and not limited thereto, in second preferred embodiment 26, for long battery life, as well as rapid and convenient battery exchange, it is contemplated for battery 56 to comprise one 9-volt alkaline battery made for performance in high tech devices. Use of a 9-volt battery 56 is also preferred as it can be so quickly and easily exchanged for a replacement by its simple insertion and withdrawal from cap 40. Hi-LED light or fiber optic light 10 is preferred for use in second preferred embodiment 26, as neither becomes hot and would not pose a risk of injurious contact with human foot 16 as it is moved into various orientation in front of reflective surface 6. FIGS. 4 and 5 each show a partially opened cover 46 connected on one of its sides to base member 24, with FIG. 4 showing a sliding cover 46 and FIG. 5 showing a cover 46 that is hinged or attached via a snap-fit connection. Also, electrical wires 34 and activation switch 32 can be seen below cover 46 in both FIG. 4 and FIG. 5. The configuration of cover 46 is not critical and not limited to that shown in FIGS. 4 and 5. Further, cover 46 could be manufactured as an independent component, or one that is permanently connected to base member 24, as long as it is sufficiently large to extend over the opening in base member 24 to seal it, and permits easy opening and closing by an operator whose hands and fingers may not be fully functional as a result of injury or disease. FIGS. 4 and 5 also show second preferred embodiment 26 having two small handles 36, each depending rearwardly from frame 4 and positioned laterally on an opposed side of base member 24. It is not contemplated for the configuration of small handles 36 to be limited to that shown in FIGS. 4 and 5, and any configuration allowing for added convenience and ease in gripping second preferred embodiment 26 is considered to be within the scope of the present invention. It is also contemplated for small handles 36 to be fixed or pivoting, angular or curved in configuration, and formed as a single unit with frame 4 or connected to frame 4 during manufacture as an attachment thereto.

FIG. 6 shows Hi-LED light 10 in the most preferred embodiment of present invention positioned substantially within hood 20, with an insulating sleeve or heat shrink material 90 securely connecting wiring leads 88 from Hi-LED light 10 to the electrical wires 34 that extend rearwardly for electrical connection to the top end 42 of battery cap 40. Hood 20 extends over the distal end of rod or tube 8, and assists in maintaining close physical contact between insulating sleeve or heat shrink material 90 and rod or tube 8. It is contemplated that Hi-LED light 10 would always remain on at approximately two percent or less power, ready for activation by operator engagement of switch 18 or 32. Hi-Led light 10 should be positioned within hood 20 a sufficient distance so that emitted light is diffused and does not directly shine in an operator's eyes when the present invention is employed to inspect foot surfaces from a standing position. Although not shown, additional insulating sleeve or heat shrink material 90 or other insulating material would be used to protect the portion of rod or tube 8 and electrical wires 34 extending between hood 20 and base member 24.

FIG. 7 shows base member 24 in the second preferred embodiment 26 of the present invention, having a rod or tube 8 connected to its top edge and positioned within an indentation 62, while rod or tube 8 supports a high intensity Hi-LED light 10 on its distal end. It is contemplated that rod or tube 8 can be rigid and fixed in configuration, or bendable into a variety of configurations and orientations by an operator (not shown). Hi-LED light 10 is substantially positioned within a hood 20, which assists in providing diffused illumination of a foot 16, or other object (not shown) or body part targeted for inspection, such as the back of an elbow or a knee, when it is placed in front of reflective surface 6. FIG. 7 also shows indentation 62 being centrally positioned within the upper edge of base member 24. Mounting the proximal end of rod or tube 8 within indentation 62 allows for closure of base member 24 against frame 4, while providing a conduit for electrical wires 34 extending between top end 42 of battery cap 40 and Hi-LED light 10. As shown in FIG. 7, electrical wires 34 are fixed firmly against rod or tube 8 between indentation 62 and Hi-LED light 10. Although providing battery cap 40 as a molded portion of base member 24 is preferred, FIG. 7 shows an alternative means of securing cap 40 against base member 24 through use of a mounting bracket 38 and fasteners 44, with the electrically active end of battery 56 fully secured within cap 40. It is contemplated for battery 56 to be located anywhere within base member 24 where adequate space exists to house it, the location and orientation being only limited by the relative sizes of battery 56 and base member 24. Fasteners 44 can be any type of screw, rivet, bolt, or other commonly used means of attachment that is appropriate to the type of materials from which base member 24 and mounting bracket 38 are made. It is not critical whether fasteners 44 comprise a single component or have multiple separable parts, even though second preferred embodiment 26, as seen in FIGS. 4 and 5, appears to have fasteners 44 comprising a single component, as not second component is visible on the back outside surface of base member 24. FIG. 7 also shows two additional electrical wires 34 extending from the micro-circuitry on the top end 42 of battery cap 40 downward toward the bottom inside surface of base member 24. The distal end of each additional electrical wire 34 is used for connection to the depressible activation switch 32, not shown in FIG. 7, that would be mounted against the semi-circular depression 60 centrally positioned within the inside front edge of base member 24. Further, the semi-circular configurations of indentation of 62 and depression 60 are not critical, and although not shown in the alternative angular cutouts or notches, or other means different from that shown in FIG. 7 can be used to secure depressible activation switch 32 within base member 24. Although some type of battery replacement access is contemplated for base member 24, for clarity of illustration none is shown in FIG. 7. Although technically possible, it is not preferred for the separation of base member 24 and frame 4 to provide the means for operator replacement of battery 56. FIG. 7 also shows one configuration of door 46 through the bottom of base member 24. However, it is equally contemplated for door 46 to be formed through any wall surface of base member 24, where it can be easily accessed.

FIGS. 8a–8f each illustrate a different configuration contemplated for the handle grip 28 in the second preferred embodiment 26 of the present invention, that depends from the distal end of elongated handle 30, to include differences in the overall shape of handle grips 281-28f, the use of grip-enhancing ridges 84 as shown on handle grips 28a–c, a strap 64 connected between handle grip 28a and elongated handle 30, and finger indentations 66. It is also contemplated for preferred embodiment 26 to comprise other conventional means of improving an operator's manipulation of elongated handle 30, for the benefit of the disabled and others not having full function of their fingers or hands. Further, it is not contemplated for the configuration of grip 28 to be limited to that shown in FIGS. 8a–8f, which are provided only by way of example. FIG. 8a shows elongated handle 30 having a generally pyramidal grip 28a, with its narrower end connected to the distal end of handle 30. FIG. 8a also shows grip-enhancing ridges 84 on the surface of pyramidal grip 28a and a strap 64 connected between pyramidal grip 28a and handle 30 to assist easy grasping, manipulation, and transport of the present invention by an operator hand (not shown) that may not be able to fully enclose around grip 28a. Use of strap 64 permits a person with arthritic hands to merely slip his or her fingers between strap 64 and handle grip 28a, instead of having to wrap fingers around grip 28 and squeeze grip 28 to lift or otherwise manipulate the present invention. FIG. 8b shows a vertically extending oblate spheroid shaped grip 28b upwardly depending from the distal end of elongated handle 30, with grip-enhancing ridges 84 being on the surface of grip 28b. FIG. 8c shows a horizontally extending oblate spheroid shaped grip 28c being connected to the distal end of elongated handle 30 and grip-enhancing ridges 84 on the surface of grip 28c, while FIG. 8d shows a spherical grip 28d connected to the distal end of elongated handle 30 without ridges 84. It is contemplated for grip-enhancing ridges to be used with any grip 28a–28f, or other configuration of handle grip 28 that is not shown but conventions in the industry for canes, umbrellas, and other devices having an elongated shaft the distal end of which is grasped by an operator during the performance of its useful function. Further, FIG. 8e shows a T-shaped grip 28e connected to the distal end of elongated handle 30 with laterally opposed finger indentations 66 on the lower surface thereof, while FIG. 8f shows the inverted J-shaped type of grip 28f, common for umbrellas (not shown), connected to the distal end of elongated handle 30. The preferred materials used for elongated handles 30 and for grips 8a–8f are lightweight, easily cleaned, durable, and devoid of a smooth, highly polished, and/or slick surface texture.

Figures 9, 10:
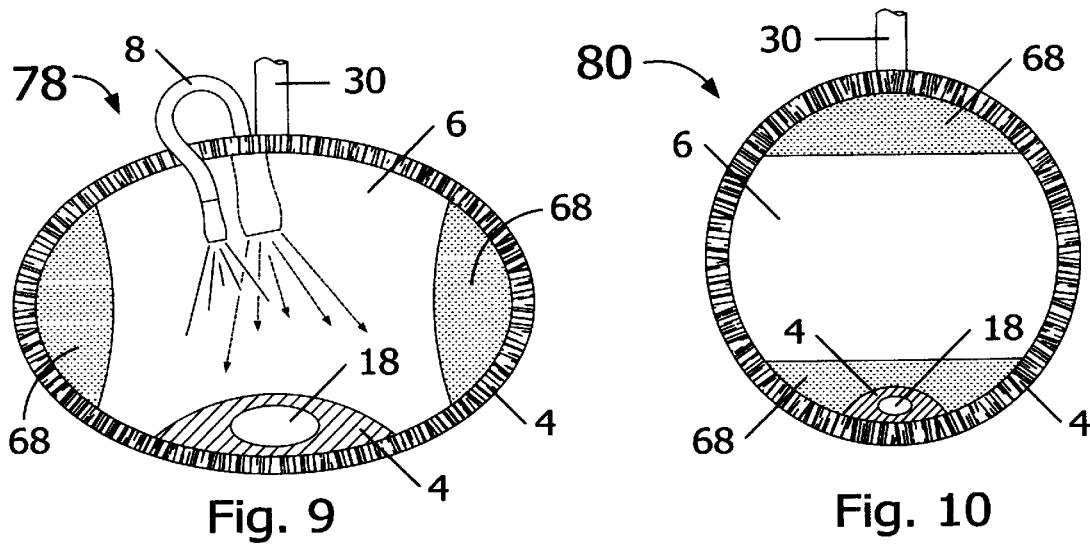
FIG. 9 is a front view of a third preferred embodiment of the present invention having an oval frame supporting a reflective surface, frosted panels on opposing sides of the reflective surface behind which at least one Hi-LED, fiber optic, or incandescent light source can be placed to created diffused light for viewing body parts including a foot, a touch switch centrally positioned through the frame below the reflective surface for activation of the lights positioned behind the frosted panels, one Hi-LED or fiber optic light connected to the distal end of a curved rod or tube, the Hi-LED light being directed to emit light in a downward position toward the reflective surface, and an elongated handle connected behind the reflective surface.
FIG. 10 is a front view of a fourth preferred embodiment of the present invention having a round frame supporting a rearwardly-inclined reflective surface, frosted panels in opposing positions respectively near to the top and bottom edges of the reflective surface and behind which at least one Hi-LED, fiber optic, or incandescent light source is placed to create diffused light for viewing body parts including a foot, and a touch switch centrally positioned through the frame below the reflective surface for activation of the lights positioned behind the frosted panels.

FIG. 9 shows a third preferred embodiment 78 of the present invention having an oval or elliptically shaped frame 4 supporting reflective surface 6, and frosted panels 68 on opposing sides of reflective surface 6 behind which at least one light source (not shown) can be placed to create diffused light for use by an operator to view his or her own body parts including a foot, such as foot 16 in FIG. 1. Although not shown, the configuration of frame 4 in third preferred embodiment 78 could be pear-shaped, or other variation of an ellipse or oval having an irregular perimeter. FIG. 9 also shows a skin-touch switch 18 centrally positioned through frame 4 below reflective surface 6 for activation of the lights positioned behind frosted panels 68. It is preferred that skin-touch switch 18 being activated by body electricity, instead of pressure exerted by contact with a portion of foot 16. Although a support structure for frame 4 is not shown in FIG. 10, it is contemplated for the oval or elliptical frame 4 to be placed into a rearwardly reclining angle relative to the floor or ground surface upon which the present invention is positioned for use by base member 24, the legs 70 and/or 72 shown in FIG. 13, or other similar and/or commonly used support means. FIG. 9 further shows elongated handle 20 connected behind frame 4. Optionally, elongated handle 30 can be detachable, foldable, telescoping, retractable, flexible, and/or have a mid-point bending strap 98, as shown in FIG. 3. Although not shown, a shorter handle configured for use in hand-manipulated inspection activity can also be substituted for elongated handle 30.

FIG. 10 shows a fourth preferred embodiment 80 of the present invention having a round frame 4 supporting reflective surface 6, frosted panels 68 in opposing positions respectively near to the top and bottom edges of reflective surface 6 and behind which at least one light source (not shown) can be placed to created diffused light for operator viewing of his or her own body parts including a foot, such as foot 16 in FIG. 1. FIG. 10 also shows a skin-touch switch 18 centrally positioned through frame 4 below reflective surface 6 for activation of the lights positioned behind frosted panels 68. It is also contemplated for the skin-touch switch 18 to be activated by the body electricity associated with the body part of the operator placed in contact with it for activation of Hi-LED or fiber optic light 10, or other light placed behind frosted panels 68. If incandescent lighting (not shown) is used behind frosted panels 68, provisions must be taken to keep the heat generated thereby from causing injury to a foot or other body part placed in close proximity to reflective surface 6. Although frosted panels 68 could be made from glass, in the most preferred embodiment it is contemplated for frost panels 68 to be made from lightweight plastic. Although a support structure for frame 4 is not shown in FIG. 10, it is contemplated for the round frame 4 to be placed into a rearwardly reclining angle relative to the floor or ground surface upon which the present invention is positioned for use by base member 24, the legs 70 and/or 72 shown in FIG. 13, or other similar and/or commonly used support means. FIG. 10 further shows elongated handle 20 connected behind frame 4. Although not shown, a shorter handle configured for use in hand-manipulated inspection activity can also be substituted for elongated handle 30 in fourth preferred embodiment 80.

Figure 11:
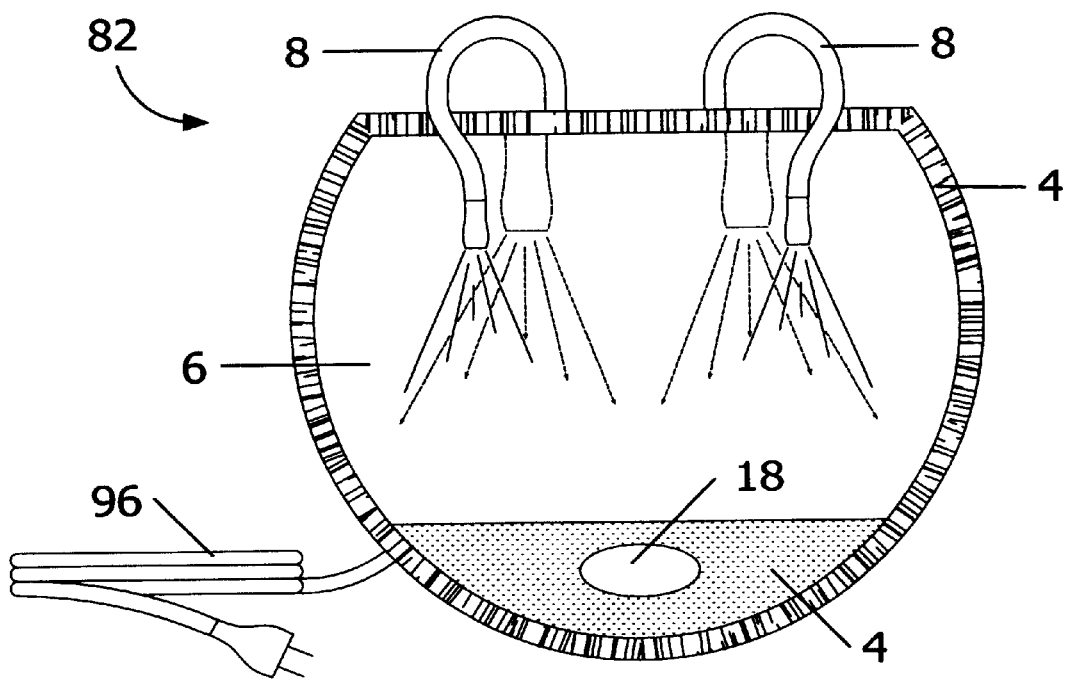
FIG. 11 is a front view of a fifth preferred embodiment of the present invention having a magnified reflective surface, a frame around the perimeter of the reflective surface, two Hi-LED or fiber optic lights the proximal end of which are attached behind the reflective surface, the lights being positioned to emit light in a downward direction toward the reflective surface, a touch switch positioned through the frame centrally below the reflective surface for activation of the lights, and a power cord connected behind the frame.

FIG. 11 shows a fifth preferred embodiment 82 of the present invention having a magnified reflective surface 6, a frame 4 around the perimeter of reflective surface 6, two Hi-LED or fiber optic lights 10 the proximal ends of which are attached behind reflective surface 6, the Hi-LED or fiber optic lights 10 being positioned to emit light in a downward direction toward reflective surface 6, a skin-touch activation switch 18 positioned through frame 4 centrally below reflective surface 6 for activation of Hi-LED or fiber optic lights 10, and a power cord and plug 96 connected behind frame 4. It is contemplated for the frame 4 shown in FIG. 11 to be placed into a rearwardly reclining angle relative to the floor or ground surface upon which the present invention is positioned for use by base member 24, the legs 70 and/or 72 shown in FIG. 13, or other similar and/or commonly used support means. Hi-LED or fiber optic lights 10 can be powered by alternating current, one or more batteries 56, or a combination there of. Further, although not shown, a cost efficient means of efficiently securing power cord and plug 96 in an out-of-the-way position when not in use is considered to be within the scope of the present invention, or in the alternative power cord and plug 96 could be retractable. Although FIG. 11 shows two Hi-LED or fiber optic lights 10 and it is contemplated that one Hi-LED or fiber optic light 10 would provide sufficient illumination for most routine inspection purposes, having more than two Hi-LED or fiber optic lights 10 is also considered to be within the scope of the present invention. In FIG. 11, power cord and plug 96 is shown to have a voltage changer at the plug, so that use in bathrooms and around other sources of water does not pose a risk of electrical shock. However, in the alternative, although not shown, it is also contemplated for the internal circuitry of the present invention to comprise a step down transformer.

FIG. 12 shows a sixth preferred embodiment 76 of the present invention having a base member 24 with a handle 36 and floor-gripping support feet 86, a front reflective surface 6, and a swivel joint 54 between base member 24 and reflective surface 6 for use in positioning reflective surface 6 into a variety of orientations relative to base member 24. Although not critical, it is contemplated for swivel joint 54 to allow pitch, yaw, and roll of reflective surface 6 relative to base member 24, and for swivel joint 54 to be able to indefinitely maintain reflective surface 6 in any operator selected orientation relative to base member 24 for as long as needed. Also, the configuration of handle 36 is not critical, and can be any configuration that is not obtrusive, as long as it provides additional means for easy movement of base member 24, and its connected reflective surface 6, into different spatial orientations relative to foot 16 and other surfaces targeted for inspection that allow for optimal viewing.

Figure 13:
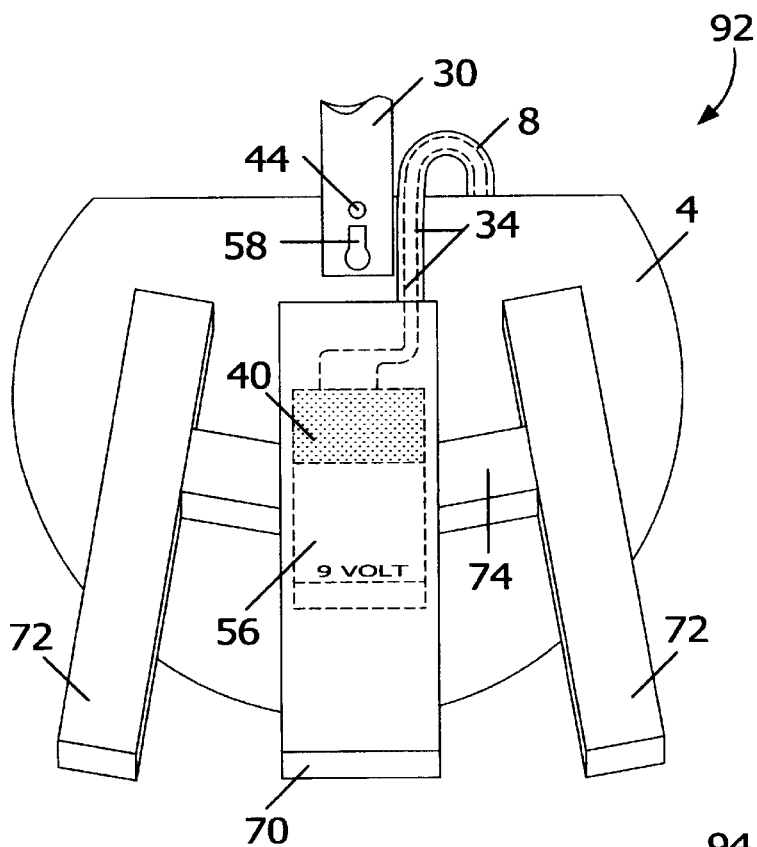
FIG. 13 is a rear view of a seventh preferred embodiment of the present invention having a frame, the proximal end of a curved rod or tube secured to the frame, the proximal end of an elongated handle connected to the top of the frame, and several legs supporting the frame with laterally extending web members connected between the legs, a battery and cap surrounding the electrically active end of the battery being housed within the central leg, and electrical wiring connected between the top of the cap and the proximal end of the curved rod or tube.

FIG. 13 shows a seventh preferred embodiment 92 of the present invention having a frame 4, the proximal end of a rod or tube 8 secured to the back of frame 4 or the top end of central leg 70, the proximal end of an elongated handle 30 connected to the top of frame 4, and one central leg 70 and two laterally positioned legs 72 supporting frame 4 in a rearwardly inclined position, with horizontally extending web members 74 connected between central leg 70 and each laterally positioned leg 72. The cross-sectional configuration of legs 70 and 72 is not critical, as long as the combination of legs 70 and 72 used provide secure support for reflective surface 6 during inspection applications. FIG. 13 also shows a battery 56 housed within central leg 70, a cap 40 also within central leg 70 and surrounding the electrically active end of battery 56, and electrical wire 34 connected between the top of cap 40 and the proximal end of rod or tube 8. Although not shown, cap 40 can be a molded part of central leg 70, or secured within central leg 70 by fasteners 44, adhesives or bonding agents, or other attachment means. Central leg 70 and laterally positioned legs 72 give an operator of the present invention additional gripping surfaces for use in moving reflective surface 6 into an optimal position of use. Also, when compared to the weight of a larger one-piece base member, such as base member 24 in FIG. 7, the combination of central leg 70, one or more laterally positioned legs 72, and web members 74 extending between legs 70 and 72, reduces the weight of the present invention, making it easier to manipulate by those with hands and/or arms weakened by injury or disease. The configuration of web members 74 is not critical, and can comprise any shape or dimension, solid or latticed, including one or more substantially parallel strips of material, that secure central leg 70 and laterally positioned legs 72 to one another. Also, the number of central legs 70 and laterally positioned legs 72 used is not critical, although at least two legs 70 or 72 are preferred to make frame 4 more resistant to movement as a result of casual contact with foot 16 when frame 4 is used upon a floor or ground surface. In contrast to the threaded stud 100 type of attachment shown in FIGS. 4 and 5, FIG. 13 shows the connection of elongated handle 30 to frame 4 being accomplished through use of an inverted T-slot 58 and fastener 44. One advantage of a connection using inverted T-slot 58 handle 30 is that the portion of the connection means attached to frame 4 would be in a more out-of-the-way position than a connection means using a threaded stud 100, and the flat-headed protrusion used with inverted T-slot 58 would extend less of a distance beyond frame 4 than threaded stud 100 and be otherwise configured so as to be less likely to cause injury to a user. The bottom end of elongated handle 30 would be tapered, or otherwise flattened, and comprise two openings therethrough, the lower opening having a T-slot 58 shaped configuration. In the alternative although not shown, an oblong connection piece with two similar openings could be attached to the proximal end of elongated handle 30. Although not clearly seen in FIG. 13, a mounting device, such as but not limited to a short flat-headed rivet attached to base member 24, would be positioned on frame 4 so as to engage inverted T-slot 58. To make the connection between elongated handle 30 and frame 4, one would simply have to slide inverted T-slot 58 down over the protrusion of frame 4 to lock T-slot 58 against the protrusion and frame 4. For a more permanent connection between elongated handle 30 and frame 4, a fastener 44 could also be used above T-slot 58 to secure elongated handle 30 and frame 4 to one another. An inverted T-slot 58 type of connection would also work for attachment of a shorter handle (not shown), when the decreased length is better suited for an intended inspection purpose.

FIG. 14 shows an eighth preferred embodiment 94 of the present invention having three adjoining magnified reflective surfaces 6 each supported by a frame 4, at least the two laterally reflective surfaces 6 each being supported by a base member 24 with all the reflective surfaces 6 being positioned at a rearwardly inclined angle relative to foot 16, for movement of foot 16 in front of reflective surfaces 6. In the alternative, it is equally contemplated for the central one of the three adjoining magnified reflective surfaces 6 to be supported by a base member 24 at an angle upwardly inclined from horizontal, whereby for inspection purposes foot 16 can moved above the three adjoining magnified reflective surfaces 6. Although not limited thereto, an upwardly inclined angle of approximately 30° could be used for efficient viewing of foot 16. FIG. 14 also shows the proximal end of a Hi-LED or fiber optic light 10 attached behind each frame 4 so that the distal ends of the Hi-LED or fiber optic lights 10 are positioned to emit light in a downward direction toward its adjacent reflective surface 6, and reflective surfaces of human foot 16 shown in each of the three reflective surfaces 6. Although no activation means is shown in FIG. 14 for Hi-LED or fiber optic lights 10, it is preferred for one activation device, such as but not limited to activation switches 18 or 32, or an optical switch, to be similarly positioned to that shown in FIGS. 2 and 3 below the central reflective surface 6, and for the single activation means to be used for activation of all three Hi-LED or fiber optic lights 10. However, even though one activation means is preferred, it is considered to be within the scope of the present invention to have an activation device, such as but not limited to activation switches 18 or 32, for each of the three Hi-LED or fiber optic lights 10 for selective operation of one or more Hi-LED or fiber optic lights 10 at a time as required by the intended application. Eighth preferred embodiment 94 is not restricted to the use of base member 24, and the legs 70 and/or 72 shown in FIG. 13, or other similar and/or commonly used support means are also contemplated. The perimeter of frame 4 is not limited to that shown in FIG. 14, and can be more rounded or have a more artistic and/or aesthetically appealing configuration. Hood 20 or the cap 22 shown in FIG. 2, can also be used with the eighth preferred embodiment 94 as needed to provide diffused light for inspection purposes. Frosted panels 68 may also be used in association with one or more of the reflective surfaces 6 in the eighth preferred embodiment 94. Although elongated handle 30 is not shown in FIG. 14, it is contemplated that the proximal end of one elongated handle 30 could be attached behind the central reflective surface 6. More than one elongated handle 30 in eighth preferred embodiment 94 would only be used where the additional weight and cost are compensated by an application benefit. Although not shown, the eighth preferred embodiment 94 could utilize one battery 56, three batteries 56, a power cord for alternating current operation, or a combination thereof.

Elongated handle 30, frame 4, small handles 36, and base member 24 can all be made from the same lightweight materials, or different materials, however, all materials used should require little or no maintenance. Also, it is contemplated for the portion of frame 4 that is below reflective surface 6 and adjacent to activation switch 18 or 32, to optionally incorporate decorative cutouts designs, graphic designs, various surface textures, and/or informational messages. Further, although not critical and not limited thereto, where the rearwardly inclined angle of reflective surface 6 is fixed relative to base member 24, legs 70 or 72, or other support means, it is contemplated for the fixed angle in the most preferred embodiment of the present invention to be approximately 35° to 40°. Where the angle between reflective surface 6 and its support means is adjustable, as in FIG. 12, viewing for foot inspection purposes is preferred between a minimum rearwardly inclined angle.of approximately 15° and a maximum rearwardly inclined angle of approximately 75°. To use the present invention for foot inspection purposes, one would first grasp elongated handle 30, small handles 36, frame 4, or a combination thereof, to conveniently position reflective surface 6 near to a foot 16. Since Hi-LED or fiber optic light 10 is continually lit at approximately two percent or less power, the present invention would be easily located in a darkened room (not shown). If adjustability of rod or tube 8 is provided as an option for the operator, rod or tube 8 would be bent into the proper curvature or otherwise adjusted to bring Hi-LED or fiber optic light 10 in close proximity to reflective surface 6 for diffused illumination of any object also placed in close proximity to reflective surface 6. For most routine inspection applications relating to a foot 16, it is contemplated for foot 16 to be placed approximately two inches from reflective surface 6. For enhanced viewing of a targeted portion of foot 16, the portion requiring closer inspection can be positioned at respective distances from reflective surface 6 that offer the optimal amount of magnification. A toe, side, heel, or other part of foot 16 would then be used to engage activation switch 18 or 32, for prompt powering up of Hi-LED or fiber optic light 10 to full illumination. If the present invention is used in a darkened room (not shown), activation switch 18 or 32 could be illuminated to facilitate operator location and engagement. Even though the present invention is light in weight, it would be expected for the combined configuration of frame 4 and base member 24 to provide a stable structure so that the present invention would not move significantly relative to foot 16 during attempts by foot 16 to engage activation switch 18 or 32, or as a result of other casual contact. During foot inspection use, an operator would move his or her own foot 16, and/or reflective surface 6, into different spatial orientations relative to the other until all of the skin surfaces needing inspection had been viewed. Should some skin surfaces remain hidden in the initially selected position into which reflective surface 6 or foot 16 is placed, elongated handle 30, small handles 36, frame 4, base member 24, or a combination thereof, could again be used to reposition reflective surface 6 relative to foot 16 for improved viewing of any previously concealed portions of foot 16. Optionally, elongated handle 30 can be detachable, foldable, telescoping, flexible, and/or have a mid-point bending strap 98, for more efficient use and storage.

What is claimed is:

1. A portable reflective device for detailed viewing of difficult to view body parts and other inspection purposes, said reflective device comprising:

at least one concave reflective surface having perimeter edges and magnification capability;

a frame surrounding said perimeter edges of each said reflective surface;

support means for each said frame configured for stabilizing said frame upon a horizontally extending surface and placing each said reflective surface in a rearwardly inclined angle of at least 15°;

high intensity lighting means secured to said support means and positioned to direct diffused light illumination against said reflective surface;

an activation switch;

micro-circuitry adapted for automatic powering down of said high intensity lighting means at a predetermined time after activation, and also adapted to permit said high intensity lighting means to remain lit at a fraction of its full power intensity between periods of activation;

power supply means; and a quantity of electrical wiring connected between said lighting means, said power supply means, and said activation switch so that when an operator engages said activation switch and places a difficult to inspect body part near to at least one said reflective surface, the operator can view the skin surfaces on the foot otherwise hidden from view without the operator having to bend into uncomfortable torso twisting positions.

2. The device of claim 1 wherein said high intensity lighting means is secured to said support means with a bendable rod having a distal end and also wherein said high intensity lighting means extends beyond said distal end to create diffused light.

3. The device of claim 1 wherein said power supply means comprises a 9-volt battery.

4. The device of claim 1 wherein said width dimension of said reflective surface is a minimum of six inches and said activation switch is illuminated.

5. The device of claim 1 further comprising an elongated handle having a proximal end and a distal end, and wherein said proximal end is connected to said base member.

6. The device of claim 5 wherein said distal end has an easily gripped configuration.

7. The device of claim 1 further comprising micro-circuitry that causes automatic deactivation of said high intensity lighting means at a pre-set time after said high intensity lighting means is engaged.

8. The device of claim 7 further comprising a cap configured for secured engagement over the electrically active end of a 9-volt battery and wherein said micro-circuitry is incorporated into said top end of said cap.

9. The device of claim 1 wherein said support means further comprises a cover configured for being moved between a closed position and opened positions.

10. The device of claim 1 wherein said high intensity lighting means is selected from a group consisting of Hi-LED lighting, fiber optic lighting, and incandescent lighting.

11. A portable mirror for detailed viewing by a human adult of difficult to view foot and other body surfaces, said mirror comprising:

at least one concave reflective surface having.perimeter edges and a magnification of approximately five times actual size;

a frame surrounding said perimeter edges of each said reflective surface;

a base member downwardly depending from said frame, said base member configured for stabilizing said frame upon a horizontally extending surface and placing said reflective surface in a rearwardly inclined minimum angle of approximately 150;

high intensity lighting means secured to said base member and positioned to direct diffused light illumination against said reflective surface;

an illuminated activation switch;

a 9-volt battery having an electrically active end;

a cap configured for engagement with said electrically active end of said battery, said cap having a top end and micro-circuitry incorporated into said top end, said micro-circuitry configured to cause automatic powering down of said high intensity lighting to a fraction of its full intensity at a pre-set time after said high intensity lighting is engaged; and a quantity of electrical wiring connected between said high intensity lighting, said power supply, and said activation switch, so that when an operator engages said activation switch and places a difficult to view body part near to said reflective surface, the operator can view all of the skin surfaces on and around the body part without having to perform bend into uncomfortable torso twisting positions.

12. The device of claim 11 wherein said width dimension of each said reflective surface is at least six inches and said activation switch is illuminated.

13. The device of claim 11 further comprising an elongated handle having a proximal end, and wherein said proximal end is attached to said base member.

14. The device of claim 13 wherein said elongated handle further comprises a distal end, and wherein said distal end has an easily gripped configuration.

15. The device of claim 11 wherein said base member has a cover configured for being moved between a closed position and opened positions, with said cover having at least a minimum size for efficient battery replacement.

16. A method of manufacture of a portable mirror for detailed viewing of difficult to view body parts, without the operator having to bend into uncomfortable torso twisting positions, said method comprising the steps of:

providing at least one reflective surface, at least one frame, at least one base member, at least one high intensity light, at least one bendable rod, at least one activation switch, at least one 9-volt battery, at least one cap configured for engagement with the electrically active end of a 9-volt battery and having a top end with incorporated micro-circuitry to cause automatic deactivation of said high intensity lighting at a pre-set time after said high intensity lighting is engaged, and a quantity of electrical wiring;

positioning each said reflective surface within said frame;

positioning each said frame upon said one of said base members so that each said combined reflective surface and frame are rearwardly inclined at a minimum angle of approximately 15°;

securing each said high intensity lighting to the distal end of one said bendable rod so that said high intensity lighting extends sufficiently beyond said distal end so as to create diffused light when activated;

securing the proximal end of each said bendable rod to said base member in a position wherein said high intensity lighting can emit diffused light against said reflective surface;

securing each said activation switch against one said base member and positioning each said activation switch whereby each said activation switch extends through said frame in a position centrally below said reflective surface;

securing said cap within said base member;

positioning the electrically active end of said 9-volt battery within said cap; and connecting said electrical wiring between said Hi-LED lighting, said power supply, and said activation switch so that engagement of said activation switch with cause power to be drawn from said battery to begin illumination of said Hi-LED lighting.

17. The method of claim 16 wherein the step of providing a reflective surface further comprises the providing of a reflective surface having a minimum width dimension of at least six inches, and further wherein the step of providing at least one activation switch further comprises the providing of activation switches that are illuminated.

18. The method of claim 16 further comprising the steps of providing an elongated handle, and securing said handle to said base member.

19. The method of claim 16 wherein said micro-circuitry is further configured to cause automatic powering down of said high intensity lighting to a fraction of its full intensity at a pre-set time after said high intensity lighting is engaged.

20. The method of claim 16 further comprising the steps of providing a base member with an opening of sufficient size for efficient battery exchange, providing a cover configured to seal said opening, and attaching said cover to said base member so that said cover can be moved between a fully opened position and a fully closed position.

* * * * *